(12) United States Patent
Gage

(10) Patent No.: US 6,239,283 B1
(45) Date of Patent: May 29, 2001

(54) PROCESS TO PREPARE CYCLIC-SULFUR FLUORINE CONTAINING OXAZOLIDINONES

(75) Inventor: James R. Gage, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/495,017

(22) Filed: Jan. 31, 2000

Related U.S. Application Data

(60) Provisional application No. 60/118,150, filed on Feb. 1, 1999.

(51) Int. Cl.$^7$ ................ C07D 335/02; C07D 409/10; C07D 413/10; C07D 263/06; C07D 269/06
(52) U.S. Cl. .................... 548/225; 548/243; 549/28; 560/9; 560/30
(58) Field of Search ............... 549/28; 548/225, 548/243; 560/30, 9

(56) References Cited

FOREIGN PATENT DOCUMENTS

| | | | |
|---|---|---|---|
| WO97/09328 | 3/1997 | (WO) | ............ C07D/413/10 |
| WO97/30995 | 8/1997 | (WO) | ............ C07D/413/10 |
| WO97/37980 | 10/1997 | (WO) | ............ C07D/263/24 |

OTHER PUBLICATIONS

"*Dehydrobenzene and Cycloalkynes*" by R.W. Hoffmann, Academic Press, N.Y., 1967. (pp. 31–33).

*Primary Examiner*—Jane C. Oswecki
(74) *Attorney, Agent, or Firm*—Bruce Stein

(57) ABSTRACT

The invention is a process for the preparation of cyclic-sulfur fluorine containing oxazolidinone antibacterial agents which utilizes the important tetrahydrothiopyran-o-fluorinated carbamate of formula (IV)

IV

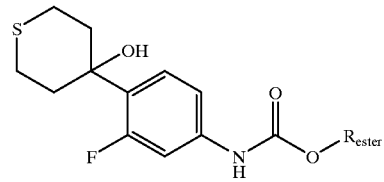

27 Claims, No Drawings

US 6,239,283 B1

PROCESS TO PREPARE CYCLIC-SULFUR FLUORINE CONTAINING OXAZOLIDINONES

CROSS REFERENCE TO RELATED APPLICATIONS

This application claims the benefit of U.S. Ser. No. 60/118,150, filed Feb. 1, 1999, under 35 USC 119(e)(i).

BACKGROUND OF THE INVENTION

1. Field of the Invention

The invention is a process for the preparation of cyclic-sulfur fluorine containing oxazolidinone antibacterial agents.

2. Description of the Related Art

Many processes are known for producing pharmaceutically antibacterial oxazolidinones, see for example, International Publication WO97/37980. However, when the the oxazolidinone contains an o-halogen substituted phenyl ring, decomposition of the metallated benzene to a reactive benzyne is a known undesirable side reaction, see "Dehydrobenzene and Cycloalkynes" by R. W. Hoffmann, Academic Press, N.Y., 1967. The process of the present invention produces a tetrahydrothiopyran-o-fluorinated oxazolidinones intermediate (IV) which is useful in producing antibacterially active oxazolidinones (XIV), (XIX) and N-[[(5S)-3-[3-fluoro-4-(tetrahydro-1-oxido-2H-thiopyran4-yl)-phenyl]-2-oxo-5-oxazolidinyl]methyl]ethanethioamide.

International Publication WO97/09328 discloses tetrahydrothiopyran-o-fluorinated oxaxolidinones which are produced by a process which requires much colder temperatures, than the claimed invention.

International Publication WO97/30995 discloses tetrahydrothiopyran-o-fluorinated oxaxolidinones which are produced by a process different that that of the present invention

SUMMARY OF INVENTION

Disclosed are tetrahydrothiopyran-o-fluorinated compounds of formula (IV)

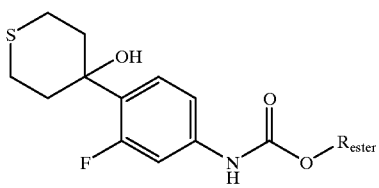

IV where $R_{ester}$ is selected from the group consisting of:
(I) $C_1$–$C_{10}$ alkyl optionally substituted with:
  (A) phenyl,
  (B) 1 thru 3 $C_1$–$C_3$ alkoxy,
(II) $C_2$–$C_5$ alkenyl optionally substituted with:
  (A) phenyl,
  (B) $C_3$–$C_7$ cycloalkyl,
(III) phenyl and optionally substituted with one thru three $C_1$–$C_3$ alkyl
(IV) naphthyl optionally substituted with one thru three $C_1$–$C_3$ alkyl.

Also disclosed are the compounds of EXAMPLES 1, 7 thru 10 and 12 thru 15.

Further disclosed is a process of preparing a tetrahydrothiopyran-o-fluorinated carbamate of formula (IV) where $R_{ester}$ is as defined above which comprises:

(1) contacting a 4-bromo-3-fluorinated carbamate of formula (II)

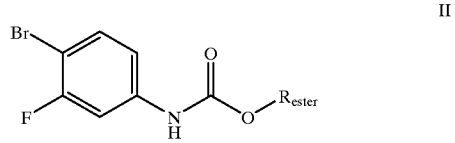

II where $R_{ester}$ is as defined above, with a Grignard reagent of the formula R—Mg—X where R is $C_1$–$C_4$ alkyl, $CH_2$=CH—, $CH_2$=CH—$CH_2$—, cyclohexyl or phenyl and where X is —Br, —Cl or —I;

(2) contacting the product of step (1) with an alkyl lithium base and (3) contacting the product of step (2) with tetrahydrothiopyran-4-one (III).

DETAILED DESCRIPTION OF THE INVENTION

The process of the present invention is the reaction of the 4-bromo-3-fluorinated carbamate (II) with tetrahydrothiopyran-4-one (III) to produce a tetrahydrothiopyran-o-fluorinated compound (IV). The tetrahydrothiopyran-o-fluorinated compound (IV) is a key intermediate to making oxazolidinone antibacterial agents which contain the tetrahydrothiopyran-o-fluorinated group.

The process starts with a 4-bromo-3-fluorinated carbamate (II). Operable $R_{ester}$ groups include:
(I) $C_1$–$C_{10}$ alkyl optionally substituted with:
  (A) phenyl,
  (B) 1 thru 3 $C_1$–$C_3$ alkoxy,
(II) $C_2$–$C_5$ alkenyl optionally substituted with:
  (A) phenyl,
  (B) $C_3$–$C_7$ cycloalkyl,
(III) phenyl and optionally substituted with one thru three $C_1$–$C_3$ alkyl and
(IV) naphthyl optionally substituted with one thru three $C_1$–$C_3$ alkyl.

It is preferred that $R_{ester}$ be $C_1$–$C_6$ alkyl or —$CH_2$—φ; it is more preferred that $R_{ester}$ be i-butyl.

The first step of the process requires that the 4-bromo-3-fluorinated carbamate (II) be reacted with a Grignard reagent of the formula R—Mg—X where R is $C_1$–$C_4$ alkyl, $CH_2$=CH—, $CH_2$=CH—$CH_2$—, cyclohexyl or phenyl and where X is —Br, —Cl or —I. It is preferred that R is $C_1$–$C_3$ alkyl or phenyl; it is more preferred that R be ethyl. It is preferred that X be —Br. This reaction is performed in the usual manner for Grignard reactions which is well known to those skilled in the art.

Step (2) is the reaction of the mixture from step (1) with an alkyl lithium base. It is preferred that the alkyl lithium base is selected from the group consisting of methyllithium, n-butyllithium, s-butyllithium and t-butyllithium. Step (2) should be performed at a temperature of less than about −15°; it is preferred that step (2) be performed at a temperature range of about −15 to about −35°, more preferably in the range of about −20 to about −35°. It is preferred that both step (1) and step (2) be performed in the presence of 3 equivalents of N,N,N',N'-tetramethylethylenediamine.

Step (3) of the process is contacting the product of step (2) with the tetrahydrothiopyran-4-one (III) to produce the desired tetrahydrothiopyran-o-fluorinated compound (IV).

It is preferred where the product of step (2) is contacted with a compound of the formula $MgQ_2$ prior to contacting with the tetrahydrothiopyran-4-one (III), where Q is —Cl, —Br or —I and where the two Qs can be the same or different prior to performing step (3). It is preferred that the two Qs be different and be —Cl and —Br.

The tetrahydrothiopyran-o-fluorinated compound (IV) is then converted to the following pharmaceutically useful antibacterial agents;

[4(S)-cis]-N-[[3-[3-fluoro-4-(tetrahydro-1-oxido-2H-thiopyran-4-yl)phenyl]-2-ox-5-oxazolidinyl]methyl] acetamide (IX) by the process of EXAMPLEs 3 thru 6,

[1α,4β(S)]-N-[[3-[3-fluoro-4-(tetrahydro-1-oxido-2H-thiopyran-4-yl)phenyl]-2-oxo-5-oxazolidinyl]methyl] propanamide monohydrate (XIV) by the process of EXAMPLEs 7 thru 11 and to 4(S)-N-[[3-[fluoro-4-(tetrahydro-1,1-dioxido-2H-thiopyran-4-yl)phenyl]-2-oxo-5-oxazolinyl]methyl] acetamide (XIX) by the process of EXAMPLEs 12 thru 16.

These three antibacterially active oxazolidinones are useful as pharmaceutical agents to treat various bacterial infections and/or diseases. For [4(S)-cis]-N-[[3-[3-fluoro-4-(tetrahydro-1-oxido-2H-thiopyran-4-yl)phenyl]-2-oxo-5-oxazolidinyl]methyl]acetamide (IX) see U.S. Patent application Ser. No. 60/100,185 (filed Sep. 14, 1998), Ser. No. 60/075,247 (filed Feb. 19, 1998) and Ser. No. 60/088, 283 (filed Jun. 5, 1998). For [1α,4β(S)]-N-[[3-[3-fluoro-4-(tetrahydro-1-oxido-2H-thiopyran-4-yl)phenyl]-2-oxo-5-oxazolidinyl]methyl]propanamide monohydrate (XIV) see U.S. patent application Ser. No. 08/696,313 (filed Aug. 13, 1996). For 4(S)-N-[[3-[fluoro-4-(tetrahydro-1,1-dioxido-2H-thiopyran-4-yl)phenyl]-2-oxo-5-oxazolinyl]methyl] acetamide (XIX) see U.S. patent application Ser. No. 60/100,185.

DEFINITIONS AND CONVENTIONS

The definitions and explanations below are for the terms as used throughout this entire document including both the specification and the claims.

I. Conventions for Formulas and Definition of Variables

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxy-carbonyl because the "$C_1$–$C_3$" refers only to the carbon atom content of the alkoxy group. Similarly while both $C_2$–$C_6$ alkoxyalkyl and ($C_1$–$C_3$)alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. Definitions

All temperatures are in degrees Centigrade.

TLC refers to thin-layer chromatography.

HPLC refers to high pressure liquid chromatography.

GC refers to gas chromatography.

Saline refers to an aqueous saturated sodium chloride mixture.

Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, chemical shifts are reported in ppm (d) downfield from TMS.

NMR refers to nuclear (proton) magnetic resonance spectroscopy, chemical shifts are reported in ppm (d) downfield from tetramethylsilane.

TMS refers to trimethylsilyl

IR refers to infrared spectroscopy.

$[a]_D^{25}$ refers to the angle of rotation of plane polarized light (specific optical rotation) at 25° with the sodium D line (589A).

MS refers to mass spectrometry expressed as m/e, m/z or mass/charge unit. $[M+H]^+$ refers to the positive ion of a parent plus a hydrogen atom. EI refers to electron impact CI refers to chemical ionization. FAB refers to fast atom bombardment.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v

Solka floc refers to an organic (cellulose) filter aid.

Ether refers to diethyl ether.

EXAMPLES

Without further elaboration, it is believed that one skilled in the art can, using the preceding description, practice the present invention to its fullest extent. The following detailed examples describe how to prepare the various compounds and/or perform the, various processes of the invention and are to be construed as merely illustrative, and not limitations of the preceding disclosure in any way whatsoever. Those skilled in the art will promptly recognize appropriate variations from the procedures both as to reactants arid as to reaction conditions and techniques.

Preparation 1

HPLC Procedure:

Column: 4.6×250 mm Zorbax RX C-8 column

Mobile Phase: A=0.1% acetic acid in water/THF (80/20); B=0.1% acetic acid in water; C=0.1% acetic acid in acetonitrile. Isocratic 50:50:0 A:B:C for 6 minutes, then gradient to 50:25:25 A:B:C over 6 minutes, then isocratic 50:25:25 A:B:C for 6 minutes, then gradient to 0:0:100 A:B:C over 6 minutes. Cycle back to 50:50:0 A:B:C.

Flow Rate: 2.5 ml/min

Wavelength: 254 nm

Retention Times: $R_t$ PNU-181497=4.0 min, $R_t$ PNU-180138=4.1

Sample Preparation: Dissolve 1 drop of the reaction mixture in 1 mL of mobile phase. Filter through a syringe filter. Inject.

Example 1

2-Methylpropyl (4-bromo-3-fluorophenyl)carbamate (II)

To a mixture of 3-fluoroaniline (I, 29.058 g, 261.5 mmol) in methylene chloride (116 ml) is added a mixture of potassium carbonate (27.26 g, 197.3 mmol, 0.75 eq) in water (116 ml) at 20–25°. The mixture is warmed to 32°, and isobutyl chloroformate (38.5 g, 282 mmol, 1.08 eq) is added over 13 min while maintaining 30–35° with mild cooling. The mixture is stirred at 30–35° for 2.5 hr until the reaction is complete to give 2-methylpropyl-(3-fluorophenyl) carbamate as determined by GC [GC method A, <0.1 area % 3-fluoroaniline; RT (3-fluoroaniline)=3.97 min, RT=14.2 min]. Aqueous ammonia (29.3 wt %, 4.20 ml, 65.0 mmol, 0.25 eq) is added and the mixture stirred at 30–35° for 15 min. The mixture is cooled to 20–25° and the pH adjusted from 8.7 to 1.9 with hydrochloric acid (37 wt %, 6.36 g, 64.5 mmol, 0.25 eq). The phases are separated and the aqueous washed with methylene chloride (58 ml). The combined organics are washed with water (118 ml) and the water wash back extracted with methylene chloride (58 ml). [In a prior experiment crystallization at this point from heptane at −30° gave 2-methylpropyl-(3-fluorophenyl)carbamate analytically pure in 98.1% yield.]. Dibromantin (57.37 g;, 200.6 mmol, 0.767 eq) and water (174 ml) are added to the combined organics and the mixture stirred at 40° for 12 hr until complete as measured by HPLC (<0.1 2-methylpropyl-(3-fluorophenyl)carbamate). The mixture is cooled to 20–25° and clarified on a "C" frit by vacuum filtration. The phases are separated and the organic (lower) phase added to a mixture of sodium sulfite (33.06 g, 262.3 mmol, 1.00 eq) in water (220 ml) with good agitation. The phases are separated and the organic phase washed with water (150 ml). Serial back-extracted the clarified solids and all aqueous with a single portion of methylene chloride (150 ml). Added heptane (520 ml) to the combined organic phases and concentrated under reduced pressure. Heptane (240 ml) is added, the mixture cooled to −30°, the precipitate is collected by vacuum filtration, washed with cold heptane (150 ml) and dried in a nitrogen stream to give the title compound; mp=79–82°; TLC $R_f$=0.41 (ethyl acetate/hexanes, 5/95); HPLC (method A) rt=6.75 min; NMR (CDCl$_3$, 400 MHz) d 7.41, 6.96, 6.87, 3.96, 1.97 and 0.96; CMR (CDCl$_3$, 75 MHz) d 159.2, 153.4, 139.0, 133.3, 115.1, 107.1, 102.0, 71.8, 27.9 and 19.0; MS (CI, NH$_3$) m/Z (relative intensity) 310 (9.3), 309 (100), 308 (6.1), 307 (100), 292 (11), 291 (18), 290 (7.5) and 289 (19)

Example 2

2-Methylpropyl [3-fluoro-4-(tetrahydro-4-hydroxy-2H-thiopyran-4-yl)phenyl]carbamate (IV)

To a solution of ethyl magnesium bromide in tetrahydrofuran (18.17 wt %, 255.36 g, 348.1 mmol, 1.19 eq) in tetrahydrofuran (145 ml) at 22° is added trimethylchlorosilane (35.4 g, 325.9 mmol) while allowing the mixture to warm to 48°. The mixture is alllowed to cool to 20–25° to give a slurry and tetrahydrofuran (152 ml) is added. In a separate flask, to a mixture of 2-methylpropyl (4-bromo-3-fluorophenyl)carbamate (II, EXAMPLE 1, 85.00 g, 293.0 mmol) and 1,10-phenanthroline monohydrate (0.5803 g, 2.927 nmol, 0.010 eq) in tetrahydrofuran (1.15 l) and N,N-tetramethylethylenediamine (103.8 g, 893 mmol, 3.05 eq) is added, while maintaining −5 to −10°, ethyl magnesium bromide in tetrahydrofuran (18.17 wt %, 243.2 g, 331.5 mmol, 1.13 eq) until the usual phenanthroline color change is obtained. The mixture is then cooled to −23 to −27° and n-butyl lithium in hexanes (162.6 g, 23.24 wt %, 590.1 mmol, 2.01 eq) is added over 1 hr while maintaining −23 to −27° and rinsed in with tetrahydrofuran (40 ml) at which point HPLC showed complete metal-halogen exchange (0.2% residual 2-methylpropyl (4-bromo-3-fluorophenyl) carbamate (II)). The mixture is cooled to −28° and the anhydrous magnesium bromide chloride slurry above is added while maintaining −28 to −19°, then rinsed in with tetrahydrofuran (56 ml). A mixture of tetrahydrothiopyran-4-one (44.39 g, 382.1 mmol, 1.30 eq) in tetrahydrofuran (100 ml) is added while maintaining less than −23°. The mixture is stirred at −23 to −27° for 45 min, then cannulated into a mixture of acetic acid (115 g, 1.915 mol, 6.54 eq) in water (570 ml) while maintaining 0–10° in the quench mixture, and rinsed with tetrahydrofuran (112 ml). The phases are separated and the organic phase is washed with a solution of ammonium chloride (43 g) in 30% aqueous ammonia (43 g) and water (570 ml) then water (570 ml). The three aqueous phases are serial back extracted with a mixture of methyl t-butyl ether (568 ml) and branched octanes (220 ml). The combined organic phases are concentrated under reduced pressure. Branched octanes (3400 ml) is added to the concentrate, and the mixture concentrated under reduced pressure, cooled to −3°, the precipitate being collected by vacuum filtration, washed with 30 branched octanes (570 ml) and dried in a nitrogen stream to give the title compound, mp=148–151°; TLC $R_f$=0.35 (ethyl acetate/hexanes, 25/75); HPLC (method A) RT=4.97; NMR (CDCl$_3$, 400 MHz) 7.38, 7.32, 7.00, 6.74, 3.96, 3.23, 2.44, 2.37, 2.05, 1.96 and 0.96 δ; CMR (CDCl$_3$, 100 MHz) 160.3, 153.5, 138.7, 129.9, 126.7, 113.9, 107.0, 71.7, 71.2, 37.7, 37.6, 28.0, 23.9 and 19.0 δ; MS (CI, NH$_3$) m/z (relative intensity) 327 (7.0), 312 (6.4), 311 (17) and 310 (100).

Example 3

2-Methylpropyl [4-(3,6-dihydro-1-oxido-2H-thiopyran-4-yl)-3-fluorophenyl]carbamate (V)

To a slurry of 2-methylpropyl [3-fluoro-4-(tetrahydro-4-hydroxy-2H-thiopyran-4-yl)phenyl]carbamate (IV, EXAMPLE 2, 64.63 g, 197.4 mmol, 90.1 wt %) in methylere chloride (194 ml) at 22° is added trifluoroacetic acid (28.0 ml, 363.5 mmol, 1.84 eq) yielding a mixture at 17° which is warmed and stirred at 35–37° for 1 hr. The mixture is cooled to 15° and a mixture of potassium carbonate (40.3 g, 292 mmol, 1.48 eq) in water (174 ml) added over 5–10 min, to control foaming, while maintaining the temperature at 15–20°. The phases are separated and the organic washed with water (100 ml). Both aqueous are serial back extracted with methylene chloride (100 ml). Methanol (500 ml) is added to the combined organic phases and the mixture concentrated under reduced pressure to give a slurry. Methanol (970 ml) is added. A mixture of sodium periodate (49.90 g, 233.3 mmol, 1.18 eq) in water (490 ml) is then added over 39 min while maintaining 23°. The slurry is stirred at 23° for 17 hr then warmed to 50° over 1 hr and stirred at 50° for 1.5 hr. The is cooled to 23° and water (733 ml) added. The slurry is cooled to −1° and the product collected by vacuum filtration, washed with water (720 ml) and dried to give the title compound, mp=212–214°; TLC $R_f$=0.43 (methanol/methylene chloride, 5/95); HPLC (method A) RT=3.58 min; NMR (DMSO-$d_6$, 400 MHz) d 9.88, 7.39,7.29–7.21, 5.78, 3.89, 3.65, 3.39–2.51, 1.93 and 0.94; CMR (DMSO-$d_6$, 100 MHz) d 159.0, 153.4, 140.1, 133.0, 129.3, 122.7, 117.7, 113.8, 105.1, 70.3, 46.2, 42.7, 27.4, 20.7 and 18.8; MS (CI, $NH_3$) m/z (relative intensity) 345 (2.9), 344 (7.9), 343 (51), 328 (13), 327 (53) and 326 (100).

Example 4 cis-2-Methylpropyl [3-fluoro-4-(tetrahydro-1-oxido-2H-thiopyran-4-yl)phenyl]carbamate (VI) and [4(R)-cis]-3-[3-Fluoro-4-(tetrahydro-1-oxido-2H-thiopyran-4-yl)phenyl]-5-(hydroxymethyl)-2-oxazolidinone (VII)

A slurry of 2-methylpropyl [4-(3,6-dihydro-1-oxido-2H-thiopyran-4-yl)-3-fluorophenyl]carbamate (V, EXAMPLE 3, 53.78 g, 165.3 mmol, 90.8 wt %) and 5% platinum on carbon (67.03% water wet, 107.61, 0.055 eq) in N,N-dimethylformamide (538 ml) is hydrogenated at 51 psig on a Parr Shaker for 23 hr at 22–29°. The hydrogen is vented and exchanged for nitrogen and the mixture heated to 63° over 2 hr The mixture is cooled and then hydrogenated at 51 psig for 20 hr at which time HPLC shows 97.5% conversion to cis-2-methylpropyl [3-fluoro-4-(tetrahydro-1-oxido-2H-thiopyran-4-yl)phenyl]carbamate (VI), mp=178–180°; TLC $R_f$=0.43 (methanol/methylene chloride, 5/95); HPLC (method A) RT=3.46 min; NMR (DMSO-$d_6$, 500 MHz) d 9.76, 7.35, 7.26–7.20, 3.88, 3.31, 3.02–2.89, 2.81, 2.51, 2.33, 1.92, 1.66 and 0.93; $^{13}$C NMR (DMSO-$d_6$, 125 MHz) d 159.5, 153.5, 139.0, 127.7, 125.8, 114.1, 105.0, 70.2, 44.9, 34.2, 27.5, 21.3 and 18.8; MS (CI, $NH_3$) m/z (relative intensity) 330 (5.2), 329 (16), 328 (79), 327 (23), 312 (20), 311 (32), 310 (39), 255 (19) and 254 (100).

The mixture is concentrated under reduced pressure while maintaining less thin 74°, then cooled to 14°. Lithium t-amylate (47.47 g, 504.6 mmol, 3.05 eq) is added with free exotherm to 26° and rinsed in with N,N-dimethylformarnide (19 ml). (S)-1,2-chloropropanediol (16.7 ml, 201 mmol, 1.22 eq) is then added over 45 min while maintaining the temperature at 30–32°. The mixture is stirred at 28–32° for 1.5 hr, then cooled to 2° and acetic acid (37.5 ml, 655 mmol, 3.96 eq) is added while keeping the temperature less than 23°. Water (225 ml) is added and the pH adjusted from 5.9 to 8.8 with aqueous ammonia (29.6 wt %, 24.36 g, 426 mmol, 2.58 eq) rinsed in with water (27 ml) while maintaining 20–25°. Solka floc (53.74 g) is added and the mixture warmed to 75°. The solids are removed by reduced pressure and washed with 64° tetrahydrofuran (805 ml), 64° methanol (625 ml), a 64° mixture of tetrahydrofuran (450 ml) and acetic acid (3.0 ml) and with 65° tetrahydrofuran (175 ml). The filtrate is concentrated under reduced pressure and extracted with methylene chloride (3×450 ml). The combined extracts are concentrated under reduced pressure and isopar-H (360 ml) is added. The mixture is then concentrated and toluene (610 ml) added to the resultant slurry. The slurry is cooled to −10° and the product collected by vacuum filtration, washed with heptane (360 ml) and dried in a nitrogen stream to give the title compound, [4(R)-cis]-3-[3-fluoro-4-(tetrahydro-1-oxido-2H-thiopyran-4-yl)phenyl]-5-(hydroxymethyl)-2-oxazolidinone (VII), mp 194–197°; TLC $R_f$=0.27 (methanol/methylene chloride, 5/95); HPLC (method B) RT=4.12 min; NMR (DMSO-$d_6$, 500 MHz) d 7.51, 7.36, 7.30, 5.21, 4.71, 4.08, 3.83, 3.69–3.66, 3.59–3.56, 3.05, 2.95, 2.82, 2.51, 2.35 and 1.68; CMR (DMSO-$d_6$, 125 MHz) d 159.5, 154.3, 138.2, 127.9, 126.9, 113.6, 104.9, 73.2, 61.6, 45.9, 44.9, 34.2, 21.3 and 21.3; MS (CI, $NH_3$) m/z (relative intensity) 345 (98), 329 (27) and 328 (100); $[ ]^{25}_D$=−40(C=0.91, DMSO).

Example 5

[4(R)-cis]-[3-[3-Fluoro-4-(tetrahydro-1-oxido-2H-thiopyran-4-yl)phenyl]-2-oxo-5-oxazolidinyl]methyl 2,5-dichlorobenzenesulfonate (VIII)

To a slurry of [4(R)-cis]-3-[3-fluoro-4-(tetrahydro-1-oxido-2H-thiopyran-4-yl)phenyl]-5-(hydroxymethyl)-2-oxazolidinone (VII, EXAMPLE 4, 48.48 g, 148.1 mmol, 84.5 wt %) in methylene chloride (417 ml) and triethylamine (40.0 ml, 287 mmol, 1.94 eq) is added 2,5-dichlorobenzenesulfonyl chloride (44.23 g, 180.2 mmol, 1.22 eq) while maintaining the temperature at 0–2°. The mixture is stirred at 2° for 5 hr then at 6° for 1 hr. The mixture is cooled to 3° and methanol (3.76 ml, 92.9 mmol, 0.63 eq) added. The mixture is stirred at 6° for 15 min then a mixture of potassium carbonate (12.33 g, 89.20 mmol, 0.60 eq) in water (239 ml) is added, followed by methylene chloride (600 ml) and water (400 ml). The mixture is warmed to 30° and the phases separated. The aqueous phase is washed with methylene chloride (200 then 100 ml) and the combined organic phases are washed with a mixture of citric acid monohydrate (62.25 g, 296.2 mmol, 2.00 eq) in water (400 ml). The citric acid phase wash is back extracted with methylene chloride (200 ml). The combined organic phases are dried over magnesium sulfate (21.35 g) and concentrated. Methanol (500 ml) is added to the concentrate and the mixture is again concentrated. Methanol (500 ml) is added to the concentrate and the mixture concentrated, cooled to −10° and the precipitate collected by vacuum filtration, washed with 0° methanol (200 ml) and dried in a nitrogen stream to give the title compound, mp=91–93° (dec); TLC $R_f$=0.57 (methanol/methylene chloride, 5/95); HPLC (method A) rt=3.93 min; NMR (DMSO-$d_6$, 400 MHz) d 8.03, 7.88, 7.79, 7.44, 7.37, 7., 4.99–4.96, 4.56–4.49, 4.16, 3.77, 3.06, 2.96, 2.83, 2.51, 2.36 and 1.69; CMR (DMSO-$d_6$, 100 MHz) d 159.0, 153.4, 137.7, 135.6, 134.1, 134.0, 132.5, 130.8, 130.3, 128.0, 127.3, 113.8, 105.1, 71.6, 69.7, 45.6, 44.9, 34.2 and 21.3; MS (CI, $NH_3$) m/z (relative intensity) 539 (2.6), 538 (1.6), 537 (4.7), 536 (1.5) and 535, (2.0); $[ ]^{25}_D$=−36 (C=0.851, DMSO) (corrected for 85.1 wt % purity).

Example 6

[4(S)-cis]-N-[[3-[3-Fluoro-4-(tetrahydro-1-oxido-2H-thiopyran-4-yl)phenyl]-2-oxo-5-oxazolidinyl]methyl]acetamide (IX)

A slurry of [4(R)-cis]-[3-[3-fluoro-4-(tetrahydro-1-oxido-2H-thiopyran-4-yl)phenyl]-2-oxo-5-oxazolidinyl]methyl 2,5-dichlorobenzenesulfonate (VIII, EXAMPLE 5, 67.69 g, 126.19 mmol, 85.1 wt %) in acetonitrile (363 ml), methanol (122 ml) and aqueous ammonia (29.6 wt %, 680 ml, 10.64 mol, 84.3 eq) at 20–25° is heated to reflux at 34° under a dry ice cooled condenser. The reaction is sealed and stirred at 40° for 19 hr. TLC shows complete conversion to [4(R)-cis]-5-(aminomethyl)-3-[3-fluoro-4-tetrahydro-1-oxido-2H-thiopyran-4-yl)phenyl]-2-oxazolidinone. The mixture is cooled to 25° and the mixture passed through an "M" fritted Buchner funnel, rinsing with water (3×75 ml). The filtrate is concentrated under reduced pressure. Acetonitrile (340 ml) and methylene chloride (440 ml) are added to the concentrate and the pH is adjusted from 8.54 to 5.07 with a mixture of citric acid monohydrate (15.80 g, 75.2 mmol, 0.596 eq) in water (29 ml). The phases are separated at 35°, and the aqueous phase is washed with a mixture of methylene chloride/acetonitrile (1/1, 2×680 ml). Methylene chloride (440 ml) is added to the aqueous and the pH adjusted to 9.0 at 22° with aqueous sodium hydroxide mixture (50 wt %, 16.57 g, 207.1 mmol, 1.64 eq). Acetic anhydride (23.3 ml, 246.9 mmol, 1.96 eq) is added and the mixture allowed to exotherm from 22 to 26°. The mixture is stirred at 24–26° for 1 hr, then the pH is adjusted from 4.34 to 8.72 with aqueous potassium carbonate (47 wt %, 162.36 g, 552 mmol, 4.38 eq). The resultant solids are removed by vacuum filtration and the phases of the filtrate separated. The solids and aqueous are serial washed with methylene chloride (3×500 ml). The combined organic phases are dried over magnesium sulfate (22.01 g) and concentrated under reduced pressure. Ethyl acetate (500 ml) is added and the resultant slurry is concentrated under reduced pressure. Ethyl acetate (500 ml) is added and the slurry concentrated under reduced pressure. The concentrate is cooled to −30° and the product collected by vacuum filtration and washed with −30° ethyl acetate (150 ml), and dried at 40° in a vacuum oven to give the title compound, mp=201–203°; TLC $R_f$=0.42 (92.3: 6.8: 0.9 methylene chloride: methanol: 29.6 wt % aqueous ammonia); HPLC (method B) RT=4.15 min; NMR (CDCl$_3$, 400 MHz) d 7.45, 7.29, 7.15–7.11, 4.83–4.78, 4.06, 3.82, 3.66, 3.14, 3.04, 2.62, 2.55, 2.03 and 1.83–1.80; CMR (CDCl$_3$, 100 MHz) d 171.5, 160.1, 154.4, 137.8, 127.8, 127.6, 113.7, 106.0, 72.1, 47.5, 46.0, 41.9, 34.8, 23.0, 21.5 and 21.5; MS (CI, NH$_3$) m/z (relative intensity) 387 (8.6), 386 (59), 370 (26) and 369 (100).

Example 7

2-Methylpropyl [3-fluoro-4-(tetrahydro-2H-thiopyran-4-yl)phenyl]carbamate (X)

To a slurry of 2-methylpropyl [3-fluoro-4-(tetrahydro-4-hydroxy-2H-thiopyran-4-yl)phenyl]carbamate (IV, EXAMPLE 2, 25.06 g, 76.54 mmol) in toluene (150 ml), hexamethyldisiloxane (48 ml, 225.84 mmol, 2.95 eq), and polymethylhydrosiloxane (27.0 ml, 452 mmol, 5.90 eq) is added a 55° mixture of anhydrous p-toluenesulfonic acid (114.3 g, 664 mmol, 8.68 eq) in toluene (100 ml) while maintaining the temperature from about 15 to about 20°. HPLC shows complete conversion to 2-methylpropyl[4-(3,6-dihydro-2H-thiopyran-4-yl)-3-fluorophenyl]carbamate. Toluene (50 ml) at 55° is used as a rinse and the mixture warmed to 72° and stirred 5.5 hr. The resultant slurry is poured into a 15° mixture of potassium carbonate (67.60 g, 489 mmol, 6.39 eq) in water (250 ml) while maintaining the temperature less than 35°. The resultant liquid phases are separated at 40° and water (150 ml) is added to the aqueous phase. The aqueous phase is washed with toluene (250 then 150 ml) and the organic phases is dried over magnesium sulfate and concentrated. Methylene chloride (200 ml) is added followed by heptane (700 ml) and the mixture concentrated. Heptane (250 ml) is added and the mixture concentrated again. The resultant slurry is cooled to −2° and the product collected by vacuum filtration, washed with cold heptane and dried in a nitrogen stream to give the title compound, TLC $R_f$=0.34 (ethyl acetate/hexanes, 10/90); HPLC (method C) RT=7.58 min; NMR (CDCl$_3$, 500 MHz) d 7.28, 7.10, 7.00, 6.78, 3.95, 2.88–2.81, 2.68, 2.09, 1.96 and 0.96; CMR (CDCl$_3$, 125 MHz) d 160.3, 153.6, 137.5, 128.1, 127.8, 114.2, 106.3, 71.5, 36.4, 33.9, 29.3, 28.0 and 19.0; MS (CI, NH$_3$) m/z (relative intensity) 312 (22), 311 (100), 255 (38), 238 (25) and 237 (85).

Example 8 trans-2-Methylpropyl [3-fluoro-4-(tetrahydro-1-oxido-2H-thiopyran-4-yl)phenyl]carbamate (XI)

To a mixture of diisopropyl L-tartrate (27.46 g, 117.23 mmol, 1.01 eq) in methylene chloride (115 ml) is added titanium (IV) isopropoxide (16.47 g, 57.95 mmol, 0.497 eq) with an exotherm from 23 to 30°. The mixture is cooled to 28° and water (1.051 g, 58.32 mmol, 0.501 eq) is added. The mixture is stirred for 10 min at 25–28° and a mixture of 2-methylpropyl [3-fluoro-4-(tetrahydro-2H-thiopyran-4-yl)phenyl]carbamate (X, EXAMPLE 7, 36.28 g, 116.50 mmol, 98.9 wt %) in methylene chloride (141 ml) is added with a methylene chloride (2×36 ml) rinse. The mixture is cooled to −21° and t-butylhydroperoxide in isooctane (2.77 M, 49.0 ml, 136 mmol, 1.17 eq) is added. The mixture is stirred at −20 to −24° for 2.5 hr, then a mixture of sodium bisulfite (6.07 g, 59.9 mmol, 0.506 eq) in water (17.9 ml) is added while maintaining the temperature at −20 to −18°. The slurry is warmed to 20–25° and methanol (165 ml) is added. The slurry is then warmed to 39° and the reaction mixture clarified through a methylene chloride wet pad of celite (36.08 g). The celite is washed with 38° methylene chloride/methanol (2/1, 2×165 ml) and the combined filtrate concentrated under reduced pressure. Methanol is added and the mixture concentrated. The slurry is cooled to −33° and the product collected by vacuum filtration, washed with −25° methanol and dried in a nitrogen stream to crude title compound. The celite/titanium dioxide cake is resuspended in 38° methylene chloride/methanol (2/1) and clarified through a methylene chloride wet pad of additional celite (16.3 g) and rinsed through with 38° methylene chloride/methanol (2/1, 165 ml). The filtrate is concentrated under reduced pressure and methanol (34.0 g) is added. The slurry is concentrated, cooled to −30°, and additional product collected by vacuum filtration, washed with −30° methanol and dried in a nitrogen stream to give the title compound, TLC $R_f$=0.38 (methanol/methylene chloride. 5/95); HPLC (method C) RT=26.15 min; NMR (DMSO-d$_6$, 400 MHz) d 9.88, 7.44, 7.38–7.27, 3.98, 3.49–3.41, 3.14–3.08, 2.90, 2.62, 2.10–1.91 and 1.04; CMR (DMSO-d$_6$, 100 MHz) d 160.1, 153.9, 143.5, 128.4, 124.8, 114.4, 105.4, 70.6, 51.5, 34.6, 29.1, 27.9 and 19.2; MS (CI, NH$_3$) m/z (relative intensity) 328 (100).

Example 9

[4(R)-trans]-3-[3-Fluoro-4-(tetrahydro-1-oxido-2H-thiopyran-4-yl)phenyl]-5-(hydroxymethyl)-2-oxazolidinone (XII)

Following the general procedure of EXAMPLE 4 and making non-critical variations but starting with trans-2-Methylpropyl [3-fluoro-4-(tetrahydro-1-oxido-2H-thiopyran-4-yl)phenyl]carbamate (XI, EXAMPLE 8, 28.30 g, 86.43 mmol, 91.1 area % purity), the title compound is obtained, TLC $R_f$=0.15 (methanol/methylene chloride, 2/98); HPLC (method B) RT=6.72 min; NMR (DMSO-d$_6$, 400 MHz) d 7.69, 7.54, 7.47, 5.40, 4.26, 4.01, 3.89–3.85, 3.78–3.74, 3.59–3.56, 3.54, 3.25–3.22, 3.01, 2.71, 2.20 and 2.08; CMR (DMSO-d$_6$, 100 MHz) d 160.1, 154.7, 138.7, 128.6, 125.9, 113.9, 105.3, 73.6, 62.0, 51.5, 46.3, 34.6 and 29.0; MS (CI, NH$_3$) m/z (relative intensity) 328 (100); $[\alpha]^{25}_D$=−38 (C=0.90, DMSO).

Example 10

[4(R)-trans]-[3-[3-Fluoro-4-(tetrahydro-1-oxido-2H-thiopyran-4-yl)phenyl]-2-oxo-5-oxazolidinyl]methyl 3-nitrobenzenesulfonate (XIII)

Following the general procedure of EXAMPLE 5, and making non-critical variations but starting with [4(R)-trans]-3-[3-Fluoro-4-(tetrahydro-1-oxido-2H-thiopyran-4-yl)phenyl]-5-(hydroxymethyl)-2-oxazolidinone (XII, EXAMPLE 9, 23.33 g, 71.26 mmol, 90.4 area % purity) and using 3-nitrobenzenesulfonyl chloride (0.16.55 g, 74.70 mmol, 1.05 eq) the title compound is obtained, TLC $R_f$=0.31 (methanol/methylene chloride, 2/98); HPLC (method A) RT=3.42 min; NMR (DMSO-$d_6$, 400 MHz) d 8.82, 8.75, 8.57, 8.19, 7.61, 7.53, 7.38–7.32, 4.76–4.68, 4.31, 3.91, 3.58, 3.55, 3.25, 3.01, 2.71, 2.21 and 2.08; CMR (DMSO-$d_6$, 100 MHz) d 160.0, 153.7, 148.4, 138.1, 136.6, 134.0, 132.3, 129.4, 126.3, 123.0, 114.1, 105.5, 71.8, 70.1, 51.5, 46.0, 34.6 and 29.0; MS (ESI) m/z (relative intensity) 513.5 (100); $[\ ]^{25}_D$=−73 (C=0.87, $CH_2Cl_2$).

Example 11

[1α,4β(S)]-N-[[3-[3-Fluoro-4-(tetrahydro-1-oxido-2H-thiopyran-4-yl)phenyl]-2-oxo-5-oxazolidinyl]methyl]propanamide monohydrate (XIV)

Following the general procedure of EXAMPLE 6 and making non-critical variations but starting with [4(R)-trans]-[3-[3-fluoro-4-(tetrahydro-1-oxido-2H-thiopyran-4-yl)phenyl]-2-oxo-5-oxazolidinyl]methyl 3-nitrobenzenesulfonate (XIII, EXAMPLE 10) and using propionic anhydride the title compound is obtained, TLC $R_f$=0.52 (475: 35: 4.8 methylene chloride: methanol: 30% aqueous ammonia); HPLC (method B) RT=10.88 min; NMR (DMSO-$d_6$, 400 MHz) d 8.15, 7.45, 7.35, 7.24, 4.10, 3.74, 3.43–3.34, 3.32, 3.08–3.02, 2.81, 2.51, 2.10, 2.00, 1.88 and 0.96; CMR (DMSO-$d_6$, 100 MHz) d 173.7, 159.6, 153.9, 138.2, 128.2, 125.7, 113.7, 105.1, 71.6, 51.0, 47.1, 41.3, 34.2, 28.6, 28.3 and 9.8; MS (CI, $NH_3$) m/z (relative intensity) 383 (100), 365 (47); IR (drift) 2920, 1744, 1672, 1627, 1533, 1513, 1483, 1423, 1330, 1232, 1205, 1187, 1135, 1030 and 756 cm-1; UV ($\Sigma_{max}$)=239 (22200, 95% ethanol); $[\ ]^{25}_D$=−21 (C=0.87, DMSO).

Example 12

2-Methylpropyl(4-(3,6-dihydro-1,1-dioxido-2H-thiopyran-4-yl)-3-fluorophenyl]carbamate (XV)

2-Methylpropyl [3-fluoro-4-(tetrahydro-4-hydroxy-2H-thiopyran-4-yl)phenyl]carbamate (IV, EXAMPLE 2, 50 g, 152.7 mmol) is slurried in 150 ml methylene chloride. Trifluoroacetic acid (21.1 ml, 274.9 mmol, 1.8 equiv.) is added and the resulting mixture is stirred at 25° for 3 hr. The reaction is quenched with 75 ml of 47% aqueous potassium carbonate and stirred at 25° for 2 hr to dissolve any salts. Water (75 ml) is added and the phases are separated. The organic layer is collected, washed with 75 ml saline followed by 75 ml water. The organic phase is then concentrated and dried under reduced pressure over night to give 2-methylpropyl[4-(3,6-dihydro-2H-thiopyran-4-yl)-3-fluorophenyl]carbamate. TLC $R_f$=0.85 (methanol/methylene chloride, 5/95); mp=99–100°; NMR ($CDCl_3$) d 7.28, 7.12, 6.99, 6.74, 5.99, 3.95, 3.33–3., 2.84, 2.63, 2.02–1.91 and 0.96; CMR ($CDCl_3$) d 159.5, 153.4, 138.4, 134.5, 129.6, 126.8, 124.0, 113.8, 106.2, 71.5, 29.3, 27.9, 25.8, 25.1 and 18.9; MS (CI, $NH_3$) m/z (relative intensity) 327 (80), 310 (100), 309(87), 281 (23), 264 (38), 235 (30), 224(33), 189 (20), 165(25) and 161 (23).

2-Methylpropyl[4-(3,6-dihydro-2H-thiopyran-4-yl)-3-fluorophenyl]carbamate in methanol (250 ml) is added to a slurry of oxone (140.8 g, 229.1 mmol, 1.5 equiv.) in a slurry of water (250 ml). Acetone (375 ml) is added to the reaction mixture and an exotherm of 30° to give 53° is noticed. The reaction mixture is stirred for 3 hr, during which time the reaction gradually cooled to 25°. The slurry is quenched with aqueous sodium bisulfite (10%, 250 ml) and stirred 1 hr. The slurry is filtered to remove salts and the cake washed with methylene chloride (250 ml) followed by water (250 ml). The filtrate is separated into two phases and the lower organic phase is collected. The aqueous phase is washed with methylene chloride (2×250 ml). The combined organic phases are washed with saline (250 ml) and then concentrated. The concentrate is dried under reduced pressure overnight to give the title compound, TLC $R_f$=0.73 (methanol/methylene chloride, 5/95); mp=147–149°; NMR ($CDCl_3$) d 7.36, 7.13, 7.03, 6.92, 5.75, 3.96, 3.80, 3.22, 3.10, 2.02–1.93 and 0.96; CMR ($CDCl_3$) d 159.5, 153.4, 139.5, 134.1, 129.5, 123.0, 119.1, 113.9, 106.2, 71.6, 50.7, 47.8, 29.2, 27.9 and 18.9; MS (CI, $NH_3$) m/z (relative intensity) 359 (100), 341 (5), 295 (18), 285 (20), 277 (23) and 178 (18).

Example 13

2-Methylpropyl[3-fluoro-4-(tetrahydro-1,1-dioxido-2H-thiopyran-4-yl)phenyl]carbamate (XVI)

Following the general procedure of EXAMPLE 4 (and using knowledge known to those skilled in the art regarding reduction of unsaturated cyclic double bonds with hydrogen) and making non-critical variations but starting with 2-methylpropyl[4-(3,6-dihydro-1,1-ioxido-2H-thiopyran-4-yl)-3-fluorophenyl]carbamate (XV, EXAMPLE 12), the title compound is obtained, TLC $R_f$=0.73 (methanol/methylene chloride, 5/95); mp=181–182°;NMR ($CDCl_3$) δ 7.36, 7.13, 7.01, 6.87, 3.95, 3.33–3.05, 2.42–2.33, 2.18, 2.01–1.94 and 0.96; CMR ($CDCl_3$) δ 159.5, 153.5, 138.4, 127.3, 124.3, 114.2, 106.2, 71.5, 51.5, 34.4, 30.1, 27.9 and 18.9; MS (CI, $NH_3$) m/z (relative intensity) 361 (100), 343 (30), 344 (10), 251(10), 243 (7) and 151(22).

Example 14

4(R)-3-[3-Fluoro-4-tetrahydro-1,1-dioxido-2H-thiopran-4-yl)phenyl]-5-(hydroxymethyl)-2-oxazolidinone (XVII)

Following the general procedures of EXAMPLEs 4 and 9 with regard to lithium t-amylate and making non-critical variations and starting with 2-methylpropyl[3-fluoro-4-(tetrahydro-1,1-dioxido-2H-thiopyran-4-yl)phenyl]carbamate (XVI, EXAMPLE 13, 38 g), the title compound is obtained, TLC $R_f$=0.44 (methanol/methylene chloride, 5/95); mp=190–193°;NMR (DMSO-$d_6$) d 7.50, 7.36, 7.29, 5.20, 4.70, 4.07, 3.82, 3.66, 3.56, 3.38–3.08, 2.15 and 2.09; CMR (DMSO-$d_6$) d 159.5, 154.3, 138.4, 128.0, 125.1, 113.5, 104.9, 73.2, 61.5, 50.4, 45.9, 33.4 and 29.9; MS (electrospray) m/z (relative intensity) 344 (100), 333 (5), 281 (5), 253(5), 180 (5) and 151(5).

Example 15

4(R)-[3-[3-Fluoro-4-(tetrahydro-1,1-dioxido-2H-thiopyran-4-yl)phenyl]-2-oxo-5-oxazolidinyl]methyl 3-nitrobenzenesulfonate (XVIII)

Following the general procedure of EXAMPLEs 5 and 10 and making non-critical variations but starting with 4(R)-3-

[3-fluoro-4-tetrahydro-1,1-dioxido-2H-thiopran-4-l)phenyl]-5-(hydroxymethyl)-2-oxazolidinone (XVII, EXAMPLE 14, 110.65 mmol) and using m-nitrobenzenesulfonyl chloride, the title compound is obtained, TLC $R_f$=0.57 (methanol/methylene chloride, 5/95); mp=185–188°; NMR (DMSO-$d_6$) δ 8.61, 8.54, 8.36, 7.96, 7.42–7.30, 7.18, 4.94, 4.50, 4.11, 3.70, 3.45–3.08, 2.15 and 2.05; CMR (DMSO-$d_6$) 159.5, 153.3, 147.9, 137.8, 136.1, 133.5, 131.9, 129.0, 128.1, 125.5, 122.5, 113.7, 105.1, 71.3, 69.7, 50.4, 45.6, 33.4 and 29.8; MS (electrospray) m/z (relative intensity) 529 (100), 353 (5), 312 (15), 304 (15), 179 (5) and 154(5).

Example 16

4(S)-N-[[3-[Fluoro-4-(tetrahydro-1,1-dioxido-2H-thiopyran-4-yl)phenyl]-2-oxo-5-oxazolinyl]methyl]acetamide (XIX)

4(R)-[3-[3-Fluoro-4-(tetrahydro-1,1-dioxido-2H-thiopyran-4-yl)phenyl]-2-oxo-5-oxazolidinyl]methyl 3-nitrobenzenesulfonate (XVIII, EXAMPLE 15, 10 g, 18.92 mmol) is slurried in acetonitrile (50 ml), methanol (20 ml) and ammoniumhydroxide (100 ml). The mixture is heated in a sealed parr bottle at 60° for 3 hs. To the resulting mixture is added potassium hydroxide (1.2 g, 21.4 mmol, 1.13 equiv.) and the mixture stirred at 25° for 1 hr. The mixture is then concentrated to dryness, using methanol to drive off residual water. Once the reaction mixture is concentrated to dryness, the solids are slurried in methylene chloride (100 ml). Acetic anhydride (4.46 ml, 47.3 mmol, 2.5 equiv.) is added and the slurry stirred at 25° for 30 minutes. TLC shows the reaction is complete and the mixture is quenched with methanol (100 ml). The salts are removed by vacuum filtration and the filtrate concentrated to approximately 50 ml. Methanol (50 ml) is added back and the slurry concentrated to 50 ml. The slurry is cooled to −20° overnight and product collected by vacuum filtration. The cake is washed with methanol and dried under reduced pressure to give the title compound, TLC $R_f$=0.32 (methanol/methylene chloride, 5/95); mp=198–199°; NMR (CDCl$_3$) δ 8.22, 7.47, 7.37, 7.26, 4.72, 4.11, 3.73, 3.42–3.08, 2.15, 2.04 and 1.83; CMR (CDCl$_3$) δ 169.9, 159.5, 153.9, 138.3, 128.1, 125.3, 113.8, 105.2, 71.6, 50.4, 47.1, 41.3, 33.4, 29.9 and 22.3; MS(electrospray), m/z (relative intensity) 402 (100), 385 (20), 322 (5), 256(5) and 212 (5).

Example 17

Benzyl-[3-fluoro-4-(tetrahydro-4-hydroxy-2H-thiopyran-4-yl)phenyl]carbamate (IV)

A mixture of 1-(3-fluorophenyl)-2,2,5,5-tetramethyl-1-aza-2,5-disilacyclopentane (14.56 g, 57.4 mmol) in dry tetrahydrofuran (230 mL) at −78° under nitrogen is treated with sec-butyllithium (1.3 M in cyclohexane, 48.6 mL, 63.1 mmol) dropwise over 5 mins, and the resulting mixture is stirred at -780 for 2 hrs. The mixture is then treated with a solution of tetrahydrothiopyran-4-one (7.00 g, 60.3 mmol) in dry tetrahydrofuran (60 mL) dropwise over 10 mins and is stirred for 3.5 hrs, during which the reaction temperature is allowed to rise to 0°. The mixture is quenched with saturated aqueous ammonium chloride (100 mL), diluted with water (100 mL), the layers are separated, the aqueous phase is extracted with ether (100 mL), and the combined organic phase is washed with saline (100 mL), dried over anhydrous sodium sulfate and concentrated under reduced pressure. The residue is then dissolved in methanol (230 mL) and treated with anhydrous potassium carbonate (15.9 g, 115 mmol), and the mixture is stirred at 20–25° for 1 hr, concentrated under reduced pressure, diluted with ether (150 mL) and water (150 mL), the layers are separated, the aqueous phase is extracted with ether (100 mL), and the combined organic phase is washed with water (50 mL) and saline (50 mL), dried over anhydrous magnesium sulfate and concentrated under reduced pressure to give the crude 3-fluoro-4-[4-(hydroxy)tetrahydrothiopyran-4-yl]benzenamine intermediate ($R_f$=0.09 by TLC, ethyl acetate/hexane (25/75)). A mixture of this intermediate and sodium bicarbonate (9.54 g, 115 mmol) in tetrahydrofuran (230 mL) and water (100 mL) is treated with benzyl chloroformate (8.2 mL, 57.4 mmol) with vigorous stirring, and the resulting mixture is stirred at 20–25° for 2 hrs. The mixture is then washed with water (2×50 mL) and saline (50 mL), dried over anhydrous sodium sulfate and concentrated under reduced pressure, the residue is then chromatographed on silica gel (230 –400 mesh, 350 g), eluting with methanol/methylene chloride (0.5/99.5), and those fractions with an $R_f$=0.15 by TLC (ethyl acetate/hexane, 25/75) are pooled, concentrated and recrystallized from ethyl acetate/hexane to give the title compound, mp=133–134°; NMR (400 MHz, CDCl$_3$) 7.37, 7.00, 6.70, 5.21, 3.23, 2.45, 2.38, 2.05 and 1.92 δ; CMR (100 MHz, CDCl$_3$) 160.5, 153.5, 138.8, 136.1, 130.5, 129.0, 128.9, 128.7, 127.0, 114.3, 107.4, 71.6, 67.7, 37.9 and 24.2; IR (mull) 3467, 3317, 1708, 1605, 1538, 1412, 1313, 1251, 1241, 1233, 1223, 1066, 855, 742, 695 cm$^{-1}$; MS (EI) m/z (rel. intensity) 361 (M+, 11), 334 (4), 333 (19), 301 (5), 300 (29), 256 (4), 228 (3), 92 (8), 91 (99), 65 (6); HRMS (EI) calculatea for $C_{19}H_{20}FNO_3S$ =361.1148, found=361.1153.

Example 18

N-[[(5S)-3-[3-Fluoro-4-(tetrahydro-1-oxido-2H-thiopyran-4-yl)-phenyl]-2-oxo-5-oxazolidinyl]methyl]ethanethioamide To a vial is added sequentially at 20–25° [4(R)-trans]-[3-[3-fluoro-4-(tetrahydro-1-oxido-2H-thiopyran-4-yl)phenyl]-2-oxo-5-oxazolidinyl]methyl 3-nitrobenzenesulfonate (XIII, EXAMPLE 10, 0.5015 g, 0.979 mmol), acetonitrile (3.30 ml), methanol (1.10 ml), and aqueous ammonia (29.8 wt %, 6.2 ml, 97.1 mmol, 99.2 eq), the vial sealed and the mixture agitated at 60° for 4.5 hr. The mixture is then concentrated under reduced pressure to 2.9 g net weight and methyl t-butyl ether (5.0 ml) is added. The organic phase is separated and discarded and the pH of the aqueous phase is adjusted from 8.1 to 12.1 with aqueous sodium hydroxyde (50% (w/v), 4 drops). Sodium chloride (498.8 mg) is added and the aqueous phase is extracted with methylene chloride (4×10 ml). The combined organics extracts are concentrated under reduced pressure. The concentrate (0.302 g) is dissolved in THF (3.5 ml) and triethylamine (0.345 ml, 2.475 mmol, 2.53 eq). Ethyl dithioacetate (0.135 ml, 1.18 mmol, 1.20 eq) is added and the mixture stirred at 20–25° for 6.5 hrs to give a slurry. Methyl t-butyl ether (5.0 ml) is added and the product collected by vacuum filtration, washed with methyl t-butyl ether (10.0 ml) and dried in a nitrogen stream to give the title compound, TLC $R_f$=0.42 (475: 35: 4.8 CH$_2$Cl$_2$: MeOH: 30% NH$_{3(aq)}$); NMR (DMSO-$d_6$, 400 MHz) δ 10.34, 7.46, 7.34, 7.24, 4.15, 3.96–3.79, 3.39–3.30, 3.08–3.03, 2.81, 2.45 and 2.02–1.84; CMR (DMSO-$d_6$, 100 MHz) δ 201.79, 160.04, 154.16, 138.52, 128.55, 126.17, 114.14, 105.62, 70.69, 51.48, 48.36, 47.58, 34.67, 33.13 and 29.02; MS (CI, NH$_3$) m/z (relative intensity) 385 (0.6), 341 (100); [ ]$^{25}_D$=0 (C 0.93, DMSO).

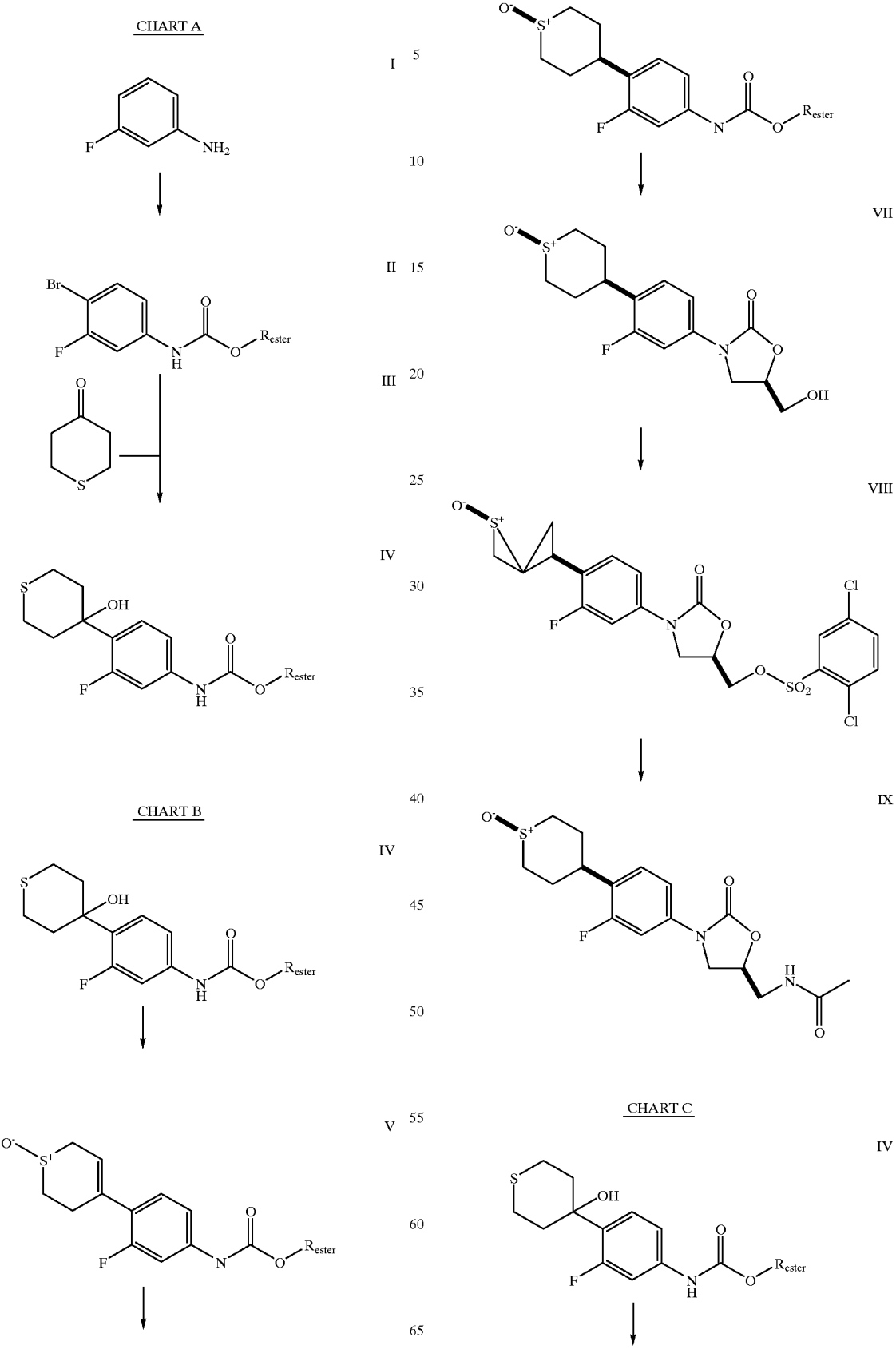

CHART D
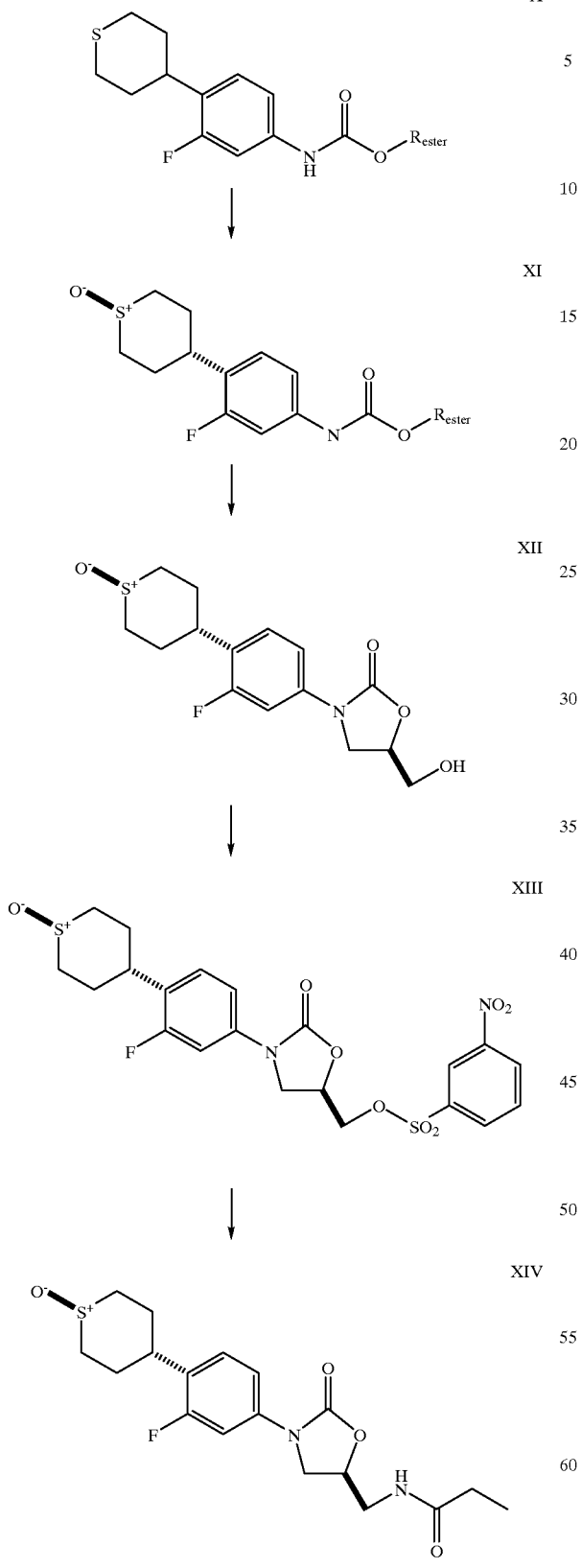
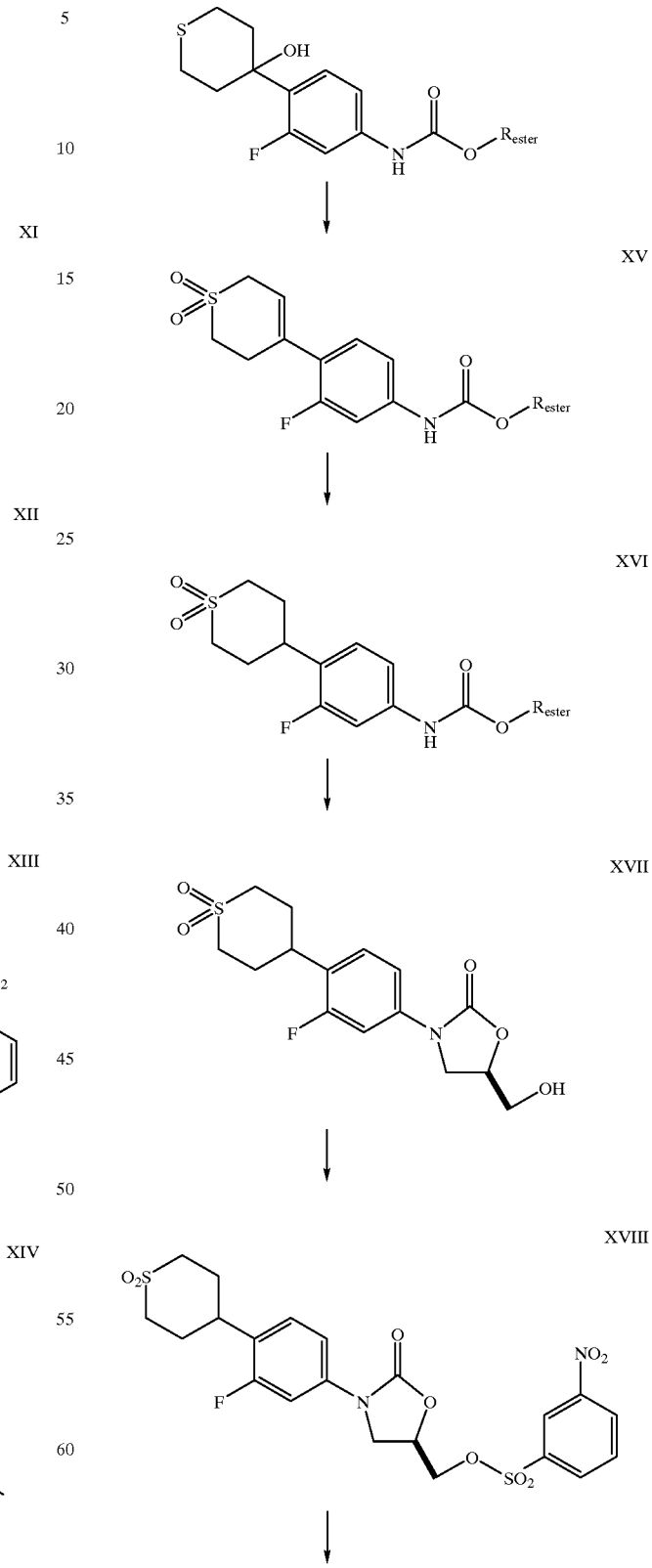

-continued

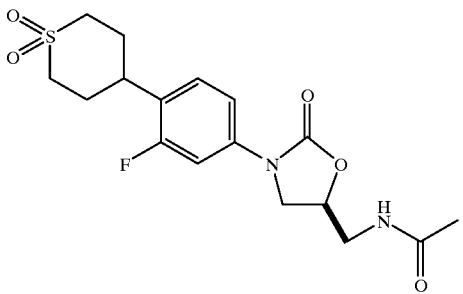

XIX

What is claimed is:

1. A fluorinated cyclic sulfur containing compound of formula (IV)

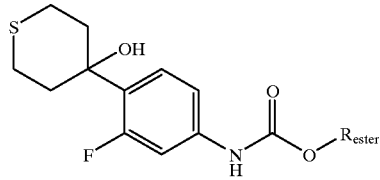

IV where $R_{ester}$ is selected from the group consisting of:
(I) $C_1$–$C_{10}$ alkyl optionally substituted with:
  (A) phenyl,
  (B) 1 thru 3 $C_1$–$C_3$ alkoxy,
(II) $C_2$–$C_5$ alkenyl optionally substituted with:
  (A) phenyl,
  (B) $C_3$–$C_7$ cycloalkyl,
(III) phenyl and optionally substituted with one thru three $C_1$–$C_3$ alkyl
(IV) naphthyl optionally substituted with one thru three $C_1$–$C_3$ alkyl.

2. A fluorinated cyclic sulfur containing compound of formula (IV) according to claim 1 where $R_{ester}$ is selected from the group consisting of:
methyl, ethyl, propyl, i-propyl, n-butyl, s-butyl, i-butyl, t-butyl, hexyl, octyl, 2-ethylhexyl,
4-butenyl, 5-pentenyl, allyl,
cyclopentyl, cyclohexyl,
phenyl, naphthyl, p-tolyl,
benzyl and
methoxyethyl.

3. A fluorinated cyclic sulfur containing compound of formula (IV) according to claim 1 where $R_{ester}$ is i-butyl and benzyl.

4. A fluorinated cyclic sulfur containing compound of formula (IV) according to claim 1 which is 2-methylpropyl-[3-fluoro-4-(tetrahydro-4-hydroxy-2H-thiopyran-4-yl)phenyl]carbamate.

5. A fluorinated cyclic sulfur containing compound of formula (IV) according to claim 1 which is benzyl-[3-fluoro-4-(tetrahydro-4-hydroxy-2H-thiopyran-4-yl)phenyl]carbamate.

6. 2-Methylpropyl (4-bromo-3-fluorophenyl)carbamate.

7. 2-Methylpropyl [3-fluoro-4-(tetrahydro-2H-thiopyran-4-yl)phenyl]carbamate.

8. trans-2-Methylpropyl [3-fluoro-4-(tetrahydro-1-oxido-2H-thiopyran-4-yl)phenyl]carbamate.

9. [4(R)-trans]-3-[3-Fluoro-4-(tetrahydro-1-oxido-2H-thiopyran-4-yl)phenyl]-5-(hydroxymethyl)-2-oxazolidinone.

10. [4(R)-trans]-[3-[3-Fluoro-4-(tetrahydro-1-oxido-2H-thiopyran-4-yl)phenyl]-2-oxo-5-xazolidinyl]methyl 3-nitrobenzenesulfonate.

11. 2-Methylpropyl[4-(3,6-dihydro-1,1-dioxido-2H-thiopyran-4-yl)-3-fluorophenyl]carbamate.

12. [1α,4β(S)]-N-[[3-[3-Fluoro-4-(tetrahydro-1-oxido-2H-thiopyran-4-yl)phenyl]-2-oxo-5-oxazolidinyl]methyl] propanamide monohydrate.

13. 4(R)-3-[3-Fluoro-4-tetrahydro-1,1-dioxido-2H-thiopyran-4-yl)phenyl]-5-(hydroxymethyl)-2-oxazolidinone.

14. 4(R)-[3-[3-Fluoro-4-(tetrahydro-1,1-dioxido-2H-thiopyran-4-yl)phenyl]-2-oxo-5-oxazolidinyl]methyl 3-nitrobenzenesulfonate.

15. A process of preparing a tetrahydrothiopyran-o-fluorinated carbamate of formula (IV)

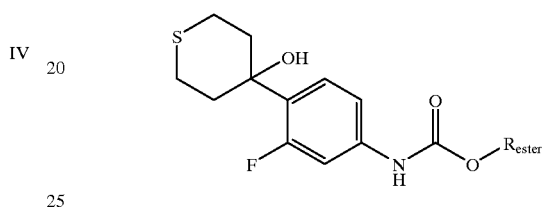

IV where $R_{ester}$ is selected from the group consisting of:
(I) $C_1$–$C_{10}$ alkyl optionally substituted with:
  (A) phenyl,
  (B) 1 thru 3 $C_1$–$C_3$ alkoxy,
(II) $C_2$–$C_5$ alkenyl optionally substituted with:
  (A) phenyl,
  (B) $C_3$–$C_7$ cycloalkyl,
(III) phenyl and optionally substituted with one thin three $C_1$–$C_3$ alkyl
(IV) naphthyl optionally substituted with one thru three $C_1$–$C_3$ alkyl which comprises:
(1) contacting a 4-bromo-3-fluorinated carbamate of formula (II)

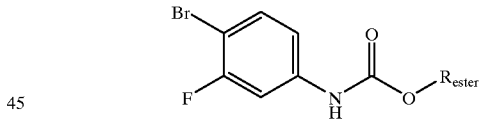

II where $R_{ester}$ is as defined above, with a Grignard reagent of the formula R—Mg—X where R is $C_1$–$C_4$ alkyl, $CH_2$=CH—, $CH_2$=CH—$CH_2$—, cyclohexyl or phenyl and where X is —Br, —Cl or —I;
(2) contacting the product of step (1) with an alkyl lithium base and
(3) contacting the product of step (2) with tetrahydrothiopyran-4-one.

16. A process of preparing a tetrahydrothiopyran-o-fluorinated carbamate of formula (IV) according to claim 15 where $R_{ester}$ is $C_1$–$C_6$ alkyl or —$CH_2$—φ.

17. A process of preparing a tetrahydrothiopyran-o-fluorinated carbamate of formula (IV) according to claim 16 where $R_{ester}$ is i-butyl.

18. A process of preparing a tetrahydrothiopyran-o-fluorinated carbamate of formula (IV) according to claim 15 where R is $C_1$–$C_3$ alkyl and phenyl.

19. A process of preparing a tetrahydrothiopyran-o-fluorinated carbamate of formula (IV) according to claim 18 where R is $C_2$ alkyl.

20. A process of preparing a tetrahydrothiopyran-o-fluorinated carbamate of formula (IV) according to claim 15 where X is —Br.

21. A process of preparing a tetrahydrothiopyran-o-fluorinated carbamate of formula (IV) according to claim 15 where the alkyl lithium base is selected from the group consisting of methyllithium, n-butyllithium, s-butyllithium, t-butyllithium and 2-ethylhexyllithium.

22. A process of preparing a tetrahydrothiopyran-o-fluorinated carbamate of formula (IV) according to claim 21 where the alkyl lithium base is n-butyllithium and t-butyllithium.

23. A process of preparing a tetrahydrothiopyran-o-fluorinated carbamate of formula (IV) according to claim 15 where the temperature is from about −35 to about −15°.

24. A process of preparing a tetrahydrothiopyran-o-fluorinated carbamate of formula (IV) according to claim 15 where the product of step (2) is contacted with $MgQ_2$ where Q is —Cl, —Br or —I where the two Qs can be the same or different.

25. A process of preparing a tetrahydrothiopyran-o-fluorinated carbamate of formula (IV) according to claim 15 where the tetrahydrothiopyran-o-fluorinated carbamate (IV) is 2-methylpropyl [3-fluoro-4-(tetrahydro-4-hydroxy-2H-thiopyran-4-yl)phenyl]carbamate.

26. N-magnesio-4-magnesio-2-methylpropyl (4-bromo-3-fluorophenyl) carbamate salt.

27. N-magnesio-4-lithio-2-methylpropyl (4-bromo-3-fluorophenyl) carbamate salt.

\* \* \* \* \*